United States Patent
Gembrowski et al.

(10) Patent No.: US 9,821,124 B2
(45) Date of Patent: Nov. 21, 2017

(54) SHARP EXTRACTOR AND METHOD OF EXTRACTING A SHARP FROM A MEDICAL DEVICE

(71) Applicant: COVENANT MEDICAL CENTER, INC., Saginaw, MI (US)

(72) Inventors: Luke M. Gembrowski, Freeland, MI (US); Robert A. Short, Goodrich, MI (US); Cedric F. A. Moreau, Neyron (FR); Michelle G. Bauer, Burt, MI (US)

(73) Assignee: Covenant Medical Center, Inc., Saginaw, MI (US)

( * ) Notice: Subject to any disclaimer, the term of this patent is extended or adjusted under 35 U.S.C. 154(b) by 37 days.

(21) Appl. No.: 14/685,451

(22) Filed: Apr. 13, 2015

(65) Prior Publication Data

US 2015/0290398 A1 Oct. 15, 2015

Related U.S. Application Data

(60) Provisional application No. 61/978,574, filed on Apr. 11, 2014.

(51) Int. Cl.
*A61M 5/32* (2006.01)
*B23P 19/02* (2006.01)

(52) U.S. Cl.
CPC ......... *A61M 5/3205* (2013.01); *B23P 19/025* (2013.01); *Y10T 29/49822* (2015.01)

(58) Field of Classification Search
CPC ............ A61M 5/3205; Y10T 29/49822; B23P 19/025

See application file for complete search history.

(56) References Cited

U.S. PATENT DOCUMENTS 1,958,941 A * 5/1934 Chapman ............... B23D 27/00
279/89

* cited by examiner

*Primary Examiner* — John C Hong
(74) *Attorney, Agent, or Firm* — John D. Wright; Dickinson Wright PLLC (57) ABSTRACT

A sharp extractor has a ram that is actuatable to move from a disengaged position to an engaged position to dislodge a sharp from a medical device, and then return back to the disengaged position. With the medical device secured in axial alignment with the ram, the actuator is actuated to move to its engaged position, whereupon the sharp is detached from the medical device. The dislodged sharp is channeled directly into a medical waste container. Upon removing the sharp from the medical device, the medical device can be treated as standard medical waste, thereby reducing the cost associated with disposal of the medical device. With the volume of the sharp being greatly reduced as a result of removal from the relatively bulky medical device, the frequency of having to dispose the sharps can be greatly reduced, thereby further reducing cost associated with the disposal of the sharps.

7 Claims, 8 Drawing Sheets

SHARP EXTRACTOR AND METHOD OF EXTRACTING A SHARP FROM A MEDICAL DEVICE

CROSS-REFERENCE TO RELATED APPLICATION

This application claims the benefit of U.S. Provisional Application Ser. No. 61/978,574, filed Apr. 11, 2014, which is incorporated herein by reference in its entirety.

BACKGROUND OF THE INVENTION

1. Technical Field

This invention relates generally to sharps in the medical industry, and more particularly to apparatus and methods for extracting sharps from medical devices.

2. Related Art

Sharps are defined by Occupational Safety and Health Standards (OSHA) as being, "any contaminated object that can penetrate the skin, including but not limited to, needles, scalpels, broken glass, broken capillary tubes, and exposed ends of dental wires," Exposure Control Plan (ECP) 1910.1030(b). The proper disposal of sharps within the medical arena is significantly more costly than the disposal of traditional, non-sharp waste or non-sharp containing medical waste, largely as a result of having to comply with federal guidelines and regulations. Accordingly, it is widely known that the proper disposal of sharps comes at a significant cost to hospitals and other medical institutions where sharps are widely present. This is particularly true and problematic in situations where the sharp, such as a relatively small needle or lancet, for example, is contained within a significantly larger container as an assembly, wherein the entire assembly must be treated and disposed of under very strict OSHA guidelines mandated for proper sharp disposal. The volume of waste created by relatively large "sharp-containing" assemblies, such as various types of containers or components thereof, for example, can require disposal of the sharp-containing assemblies on a daily basis, particularly within institutions where high volume usage of the sharp-containing assemblies is high, which can prove to be very costly. Contributing to the cost of disposal of contaminated medical waste is the need to first sterilize the waste and then have it comminuted into small pieces. Further yet, in addition to the cost placed on the medical institution as a result of having to properly dispose of the contaminated, sharp-containing medical waste is an inherent cost that is placed on the environment in that the comminuted material from the sharp container assemblies is typically sent to landfills. A further complicating issue related to the disposal of sharps is an OSHA regulation that prevents persons from having direct physical contact with the sharp.

An example of a sharp container assembly that has proven costly to properly dispose under the strict OSHA regulations is a urine sample container assembly. The urine sample container assembly includes a plastic reservoir and a lid assembly. The lid assembly typically includes a plastic lid portion with a sharp attached thereto to facilitate obtaining a sample of the urine from the reservoir. The sharp is generally in the form of a needle that is attached within a funnel portion of the lid that depends into the reservoir upon fastening the lid assembly to the reservoir. A protective rubber sheath typically covers the needle for sterilization and protection purposes. When a urine sample is needed from the reservoir, a vacuum sealed vial having a rubber seal cover is pressed onto the needle such that the needle punctures the rubber seal cover, whereupon the vacuum within the vial causes a sample of urine to be drawn into the vial. With the sample procured in the vial, the vial is withdrawn from the needle, whereupon the urine sample container assembly can be discarded. However, due to the lid assembly having the sharp attached thereto, the entire lid assembly must be treated as a sharp, and thus, must be disposed of under the costly measures associated with the disposal of sharps. Of course, given the lid occupies a substantially greater volume than the needle alone, the total volume of the "sharp containing" assembly is dramatically increased. As a result of the volume of the lid assemblies, frequent and regularly scheduled disposal of the "sharp containing" lid assemblies, such as daily, by properly licensed, relatively high cost medical waste disposal personnel, as compared to standard, non-sharp containing waste disposal personnel, is often required in medical facilities.

SUMMARY OF THE INVENTION

In accordance with one aspect of the invention, a sharp extractor is provided. The sharp extractor has an actuator operably coupled to a ram that is actuatable to move between a disengaged position and an engaged position. With a medical device securely located in alignment with the ram, the actuator is actuated to move the ram to its engaged position, whereupon a sharp, attached to the medical device, is detached from the medical device under a force applied by the ram. The sharp is channeled into a medical waste container, whereupon the sharp can be properly disposed without concern of injury or contamination. The sharp extractor can be operated simply and efficiently such that a single person, and more preferably, a single hand, can actuate the sharp extractor to extract the sharp from the medical device. At no time during extraction of the sharp from the medical device and containment of the sharp within the medical waste container does the operator need to make physical contact with the sharp, thereby eliminating any possibility for injury or contamination from the sharp. Further yet, upon locating the medical device on the sharp extractor, the operator does not need to physically contact the medical device throughout the sharp removal process, as the medical device is securely held on the sharp extractor, thereby ensuring the operator's hands remain clear from the medical device. Upon removing the sharp from the medical device and containing the sharp within the medical waste container, the medical device can be removed from the sharp extractor and treated thereafter as standard medical waste, thereby greatly diminishing the cost associated with disposal of the medical device. Of course, with the volume of the sharp being drastically diminished as a result of removing the sharp from the relatively bulky medical device, the frequency of having to dispose the sharps can be drastically reduced, thereby lending to further reduction in cost associated with the disposal of the sharps.

A sharp extractor for removing a sharp from a medical device, constructed in accordance with one embodiment of the invention, has a base with a through opening and a tubular locator extending upwardly from the base in coaxial alignment with a central axis of the through opening. The extractor further includes an elongate ram and an actuator. The ram extends between first and second ends, with the ram being operably attached to the actuator. The ram is moveable along the central axis from a disengaged position to an engaged position in response to actuation of the actuator. The second end of the ram is axially spaced from the sharp while the actuator is in the disengaged position and is engageable with the sharp when the actuator is moved toward the engaged position, whereupon the elongate ram engages the sharp and causes the sharp to be forcibly removed from the medical device and discharged into a medical waste container.

In accordance with another aspect of the invention, a discharge chute extends from the through opening in the base to the medical waste container.

In accordance with another aspect of the invention, the actuator is a manually actuatable lever operably connected to the ram via pivotal links.

In accordance with another aspect of the invention, the discharge chute has a telescopic wall to facilitate connecting the discharge chute with the medical waste container.

In accordance with another aspect of the invention, a sharp extractor configured to remove a needle assembly from a specimen reservoir assembly is provided. The specimen reservoir assembly includes a reservoir and a lid assembly. The lid assembly includes the needle assembly and a lid portion configured for sealed attachment to the reservoir. The sharp extractor has a base with a through opening extending about a central axis and a tubular locator extending upwardly from the base in coaxial alignment with the central axis. The sharp extractor has an elongate ram that extends between first and second ends and an actuator operably attached to the ram. The ram is moveable along the central axis from a disengaged position to an engaged position in response to actuation of the actuator. The second end of the elongate ram is axially spaced from the needle assembly in the disengaged position and is engageable with the needle assembly when moved toward the engaged position whereupon the elongate ram engages the needle assembly and causes the needle assembly to be forcibly detached from the lid.

In accordance with another aspect of the invention, a tubular discharge chute extends downwardly from the through opening of the base. The needle assembly, upon being detached from the lid, travels through the discharge chute into the medical waste container.

In accordance with another aspect of the invention, a method of detaching a needle assembly from a medical device is provided. The method includes disposing the medical device on an upstanding tubular locator; actuating an elongate ram to move from the ram from a disengaged position spaced from the needle assembly toward a position engaged with the needle assembly; and causing the needle assembly to be forcibly detached from the medial device under force applied by the elongate ram, whereupon the needle assembly is disposed through the tubular locator.

In accordance with another aspect of the invention, the method further includes channeling the detached needle assembly through a discharge chute into a medical waste container.

In accordance with another aspect of the invention, the method further includes manually actuating the elongate ram via a pivotable lever.

In accordance with another aspect of the invention, the method further includes causing the elongate ram to move along a central axis of the through opening while moving the ram from the disengaged position into the engaged position with the needle assembly.

In accordance with another aspect of the invention, the method further includes extending the elongate ram through a funnel-shaped portion of the medical device prior to engaging the needle assembly.

BRIEF DESCRIPTION OF THE DRAWINGS

These and other aspects, features and advantages of the present invention will become more readily appreciated when considered in connection with the following detailed description of presently preferred embodiments and best mode, appended claims and accompanying drawings, in which:

DETAILED DESCRIPTION OF PRESENTLY PREFERRED EMBODIMENTS

Figure 4:
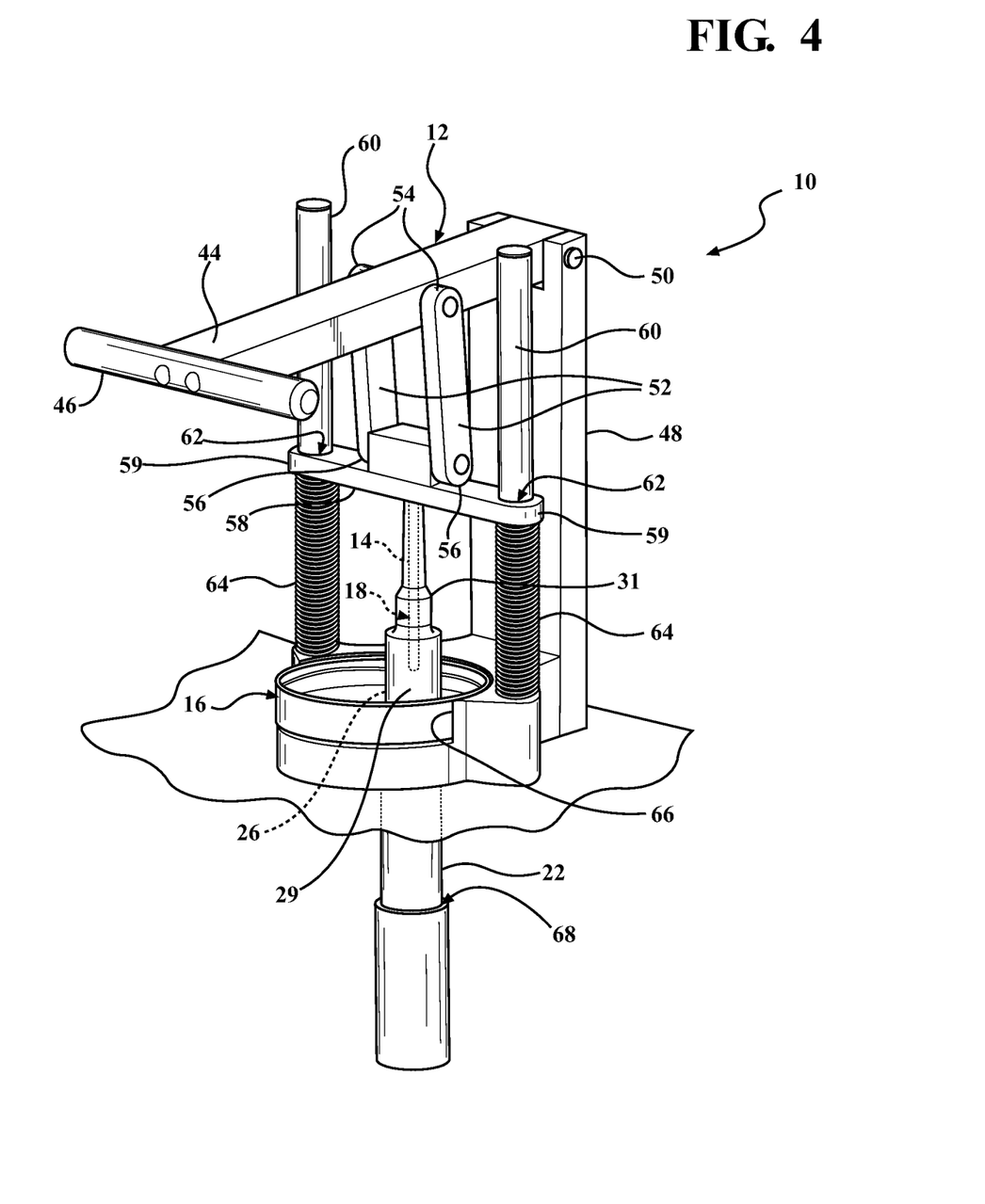
FIG. 4 is a perspective view of the sharp extractor of FIG. 1 shown in an engaged state.
Figure 5:
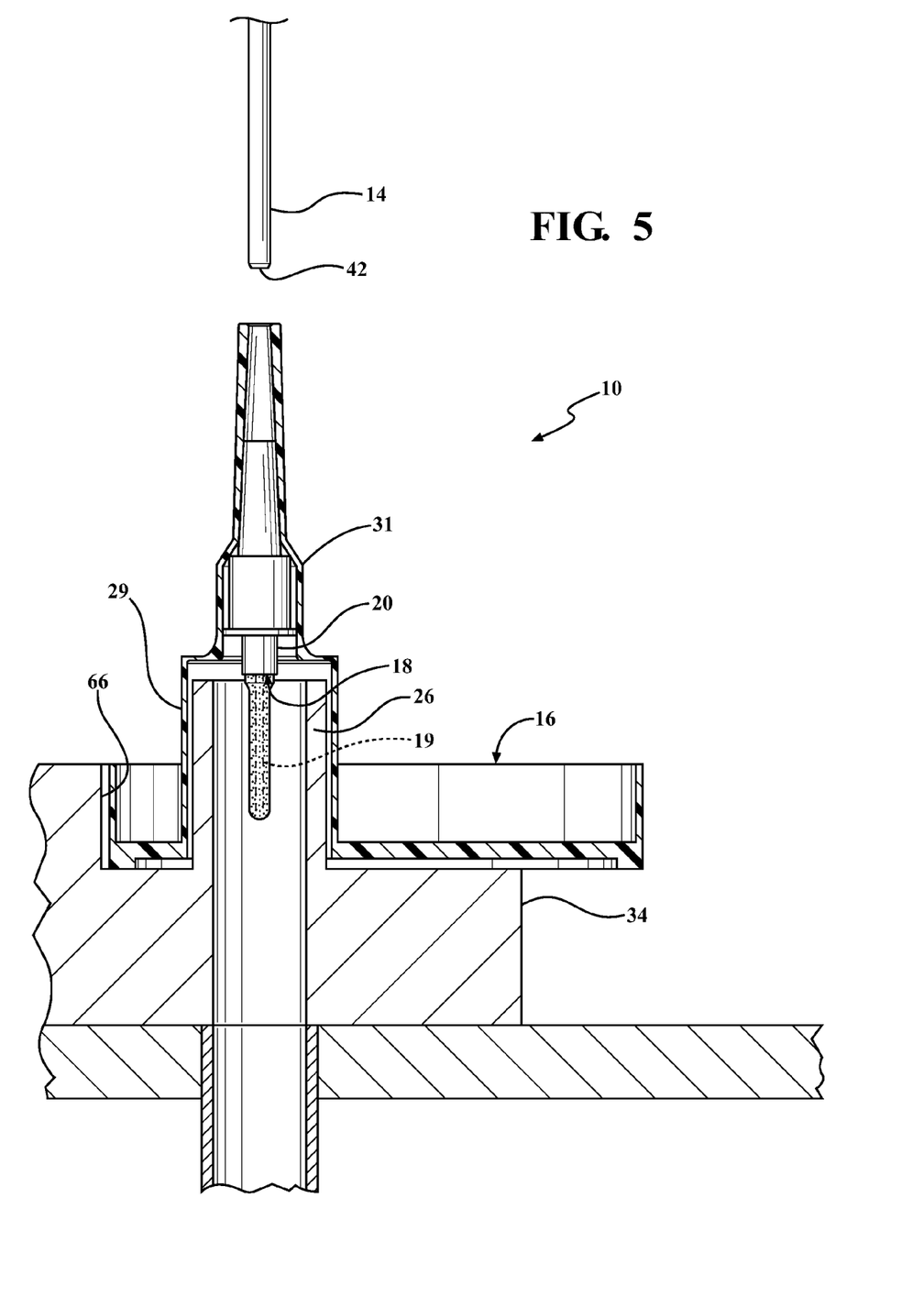
FIG. 5 is an enlarged cross-sectional side view of the sharp extractor of FIG. 1 shown in a disengaged state.
Figure 6:
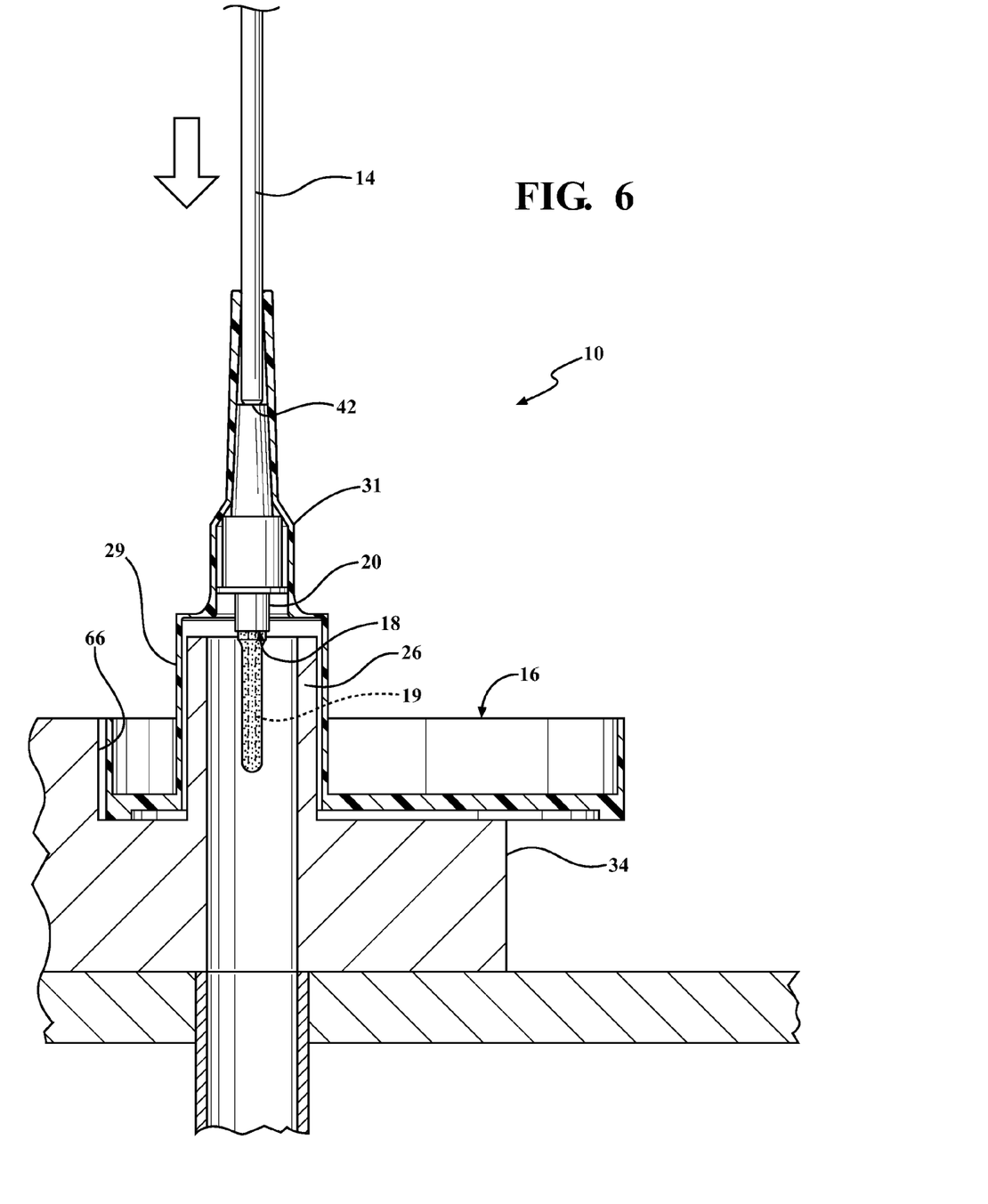
FIG. 6 is an enlarged cross-sectional side view of the sharp extractor of FIG. 1 shown in an engaged state.

Referring in more detail to the drawings, FIGS. 1-6 illustrate a sharp extractor 10 constructed in accordance with one presently preferred embodiment of the invention. The sharp extractor 10 has an actuator 12 operably coupled to an elongate punch, also referred to as ram 14, that is actuatable to move between a disengaged position (FIGS. 1-3 and 5) and an engaged position (FIGS. 4 and 6). With a sharp containing medical device 16, such as a lid assembly of a urine specimen reservoir assembly (FIGS. 8 and 9A-9B), by way of example and without limitation, securely located in axial alignment with the ram 14, the actuator 12 can be actuated to move the ram 14 to its engaged position. During movement of the ram 14 to its engaged position, a sharp 18, such as a needle assembly including a needle 19 fixed to a housing 20 (FIG. 10), is forcibly detached from the medical device 16 under a force applied by the ram 14, as shown on FIG. 6A. In accordance with a further aspect of the invention, the sharp 18 can be channeled through a discharge tube, also referred to as discharge chute or simply chute 22, into a standard sharp medical waste container 24, whereupon the sharp 18 can be properly disposed.

The sharp extractor 10 can be operated simply and efficiently by a single person, and more preferably, by a single hand. In addition, at no time does the operator need to make physical contact with the sharp 18 throughout the entire process of removing the sharp 18 up to the time of containment of the sharp 18 within the medical waste container 24, thereby preventing the possibility of injury to the operator or contamination from the sharp 18. Further yet, upon locating the medical device 16 on the extractor 10, the operator does not need to make physical contact with the medical device 16 throughout the sharp removal process. Accordingly, at no time do human hands need to made physical contact with the sharp 18 during the sharp removal process. This is made possible due to the medical device 16 being securely held and maintained on the extractor 10 by an upstanding tubular locator 26, thereby keeping the operator's hands free and clear from the medical device 16. With the sharp 18 safely removed from the medical device 16 and contained within the medical waste container 24, the medical device 16 can be simply removed from the extractor 10 and treated as standard medical waste and not a sharp, thereby greatly diminishing the cost associated with disposal of the non-sharp containing portion of the medical device. A main contributor to the reduction in the total disposal cost is due to the volume of the sharp 18 being drastically reduced via removal of the relatively small sharp 18 from the relatively large medical device 16.

Figure 7:
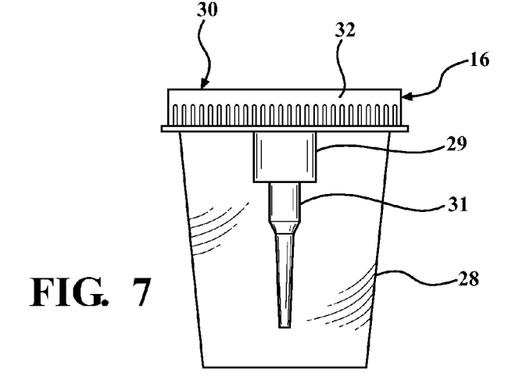
FIG. 7 is a side view of a specimen reservoir assembly.
Figure 8:
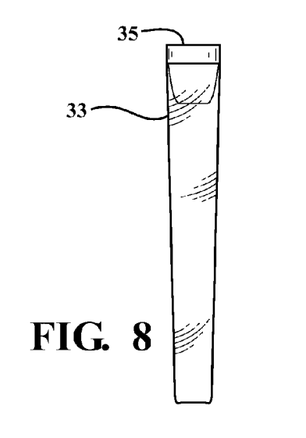
FIG. 8 is a side view of a specimen vacuum vial.
Figure 9A:
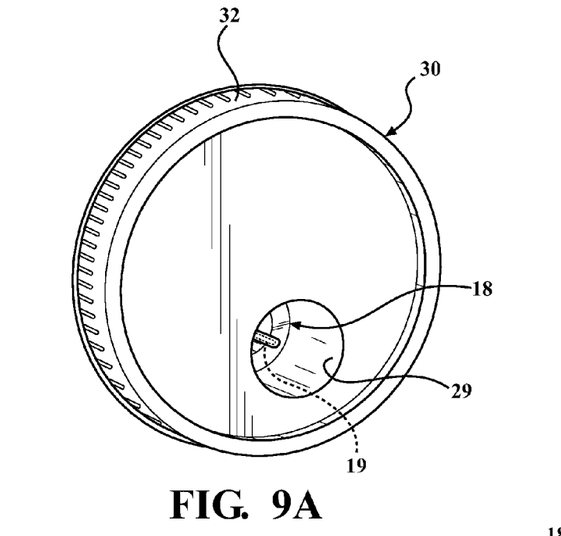
FIGS. 9A and 9B are perspective views of a lid assembly of the specimen reservoir assembly of FIG. 7.
Figure 9B:
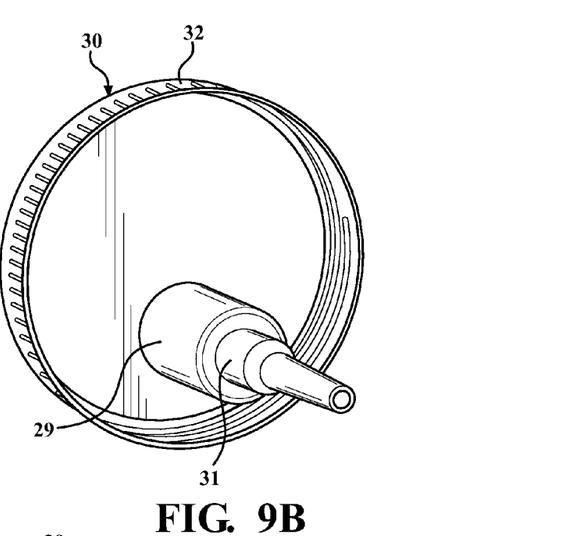
Figure 10:
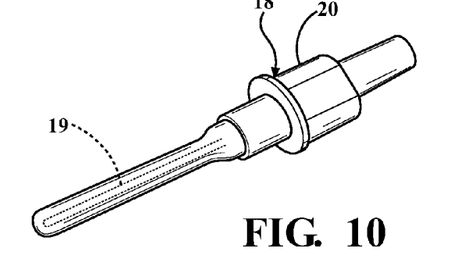
FIG. 10 is a perspective view of a sharp shown removed from the lid assembly of FIGS. 9A and 9B.

As best shown in FIG. 7, the medical device, shown as a specimen reservoir assembly 16, by way of example and without limitation, is shown having a reservoir portion, also referred to as reservoir 28, and a lid assembly 30. As best shown in FIGS. 9A and 9B, the lid assembly 30 includes a lid portion 32 with the sharp 18 releasably attached thereto within a cylindrical recessed portion 29 that extends to a generally funnel-shaped portion 31, wherein the housing 20 of the sharp 18 is fixed within a segment of the funnel-shaped portion 31. The sharp 18 is releasably fixed within the cylindrical recessed portion 29 via any suitable mechanism, such as via a press fit and/or adhesive, for example. The lid assembly 30 is configured to be attached to the reservoir 28 in fluid tight sealed fashion, such as via threaded attachment, as known. Specimen reservoir assemblies 16 as described and illustrated are typically designed for use with specimen vacuum type vials 33, such as shown in FIG. 8. Vacuum type vials 33 typically have an elastomeric cap 35 sealed to a rigid body of the vial, wherein the cap 35 can be readily and selectively punctured by the needle 19, whereupon a sample of the fluid specimen within the reservoir 28 is drawn into the vial 33 via negative vacuum pressure within the vial 33. Upon attaining the desired fluid sample within the vial 33, the medical device 16 is generally no longer needed and is typically disposed. During disposal of the medical device 16, generally the lid assembly 30 is removed from the reservoir 28 and is treated as a sharp, given the sharp 18 is attached to the lid portion 32, and the reservoir 28 is discarded as standard, non-sharp containing medical waste. The invention herein, which allows the sharp 18 to be reliably, quickly and safely removed from the lid portion 32, allows that lid portion 32, with the sharp 18 removed therefrom, to be treated as standard medical waste, while limiting the treatment of sharp waste solely to that of the needle assembly 18.

The sharp extractor 10 has a base 34 with a through opening 36 extending along a central axis 38. The tubular locator 26 extends upwardly from the base 34 in coaxial alignment with the central axis 38. The tubular locator 26 is shown as being generally cylindrical, having an outer diameter sized for a close fit, such as line-to-line or slight clearance fit, within the cylindrical recessed portion 29 of the lid assembly 30. The elongate ram 14 extends between a first end 40 and a free second end 42, wherein the actuator 12 is operably attached to the first end 40 of the ram 14, such as via any suitable mechanical attachment and/or weld joint, by way of example and without example. The actuator 12 is moveable to move the ram 14 generally along the central axis 38 from a disengaged position (FIGS. 1-3 and 5) to an engaged position (FIGS. 4 and 6). The second end 42 of the ram 14 remains axially spaced from the needle assembly 18 in the disengaged position and is brought into engagement with the needle assembly 18 when moved into the engaged position, whereupon the ram 14 causes the needle assembly 18 to be forcibly detached from the lid portion 32 and safely contained within the medical waste container 24. The elongate ram 14 is shown as being an elongate, generally cylindrical rod, wherein the outer diameter of the rod is sized for receipt within the passage of the funnel-shaped portion 31. As the elongate ram 14 is extended through the funnel-shaped portion 31, the free second end 42 of the rod is caused to engage the housing 20 of the needle assembly 18, thereby forcibly pressing the housing 20, along with the needle 19 that is fixed thereto, out of the cylindrical recessed portion 29 of the lid portion 32.

Figure 1:
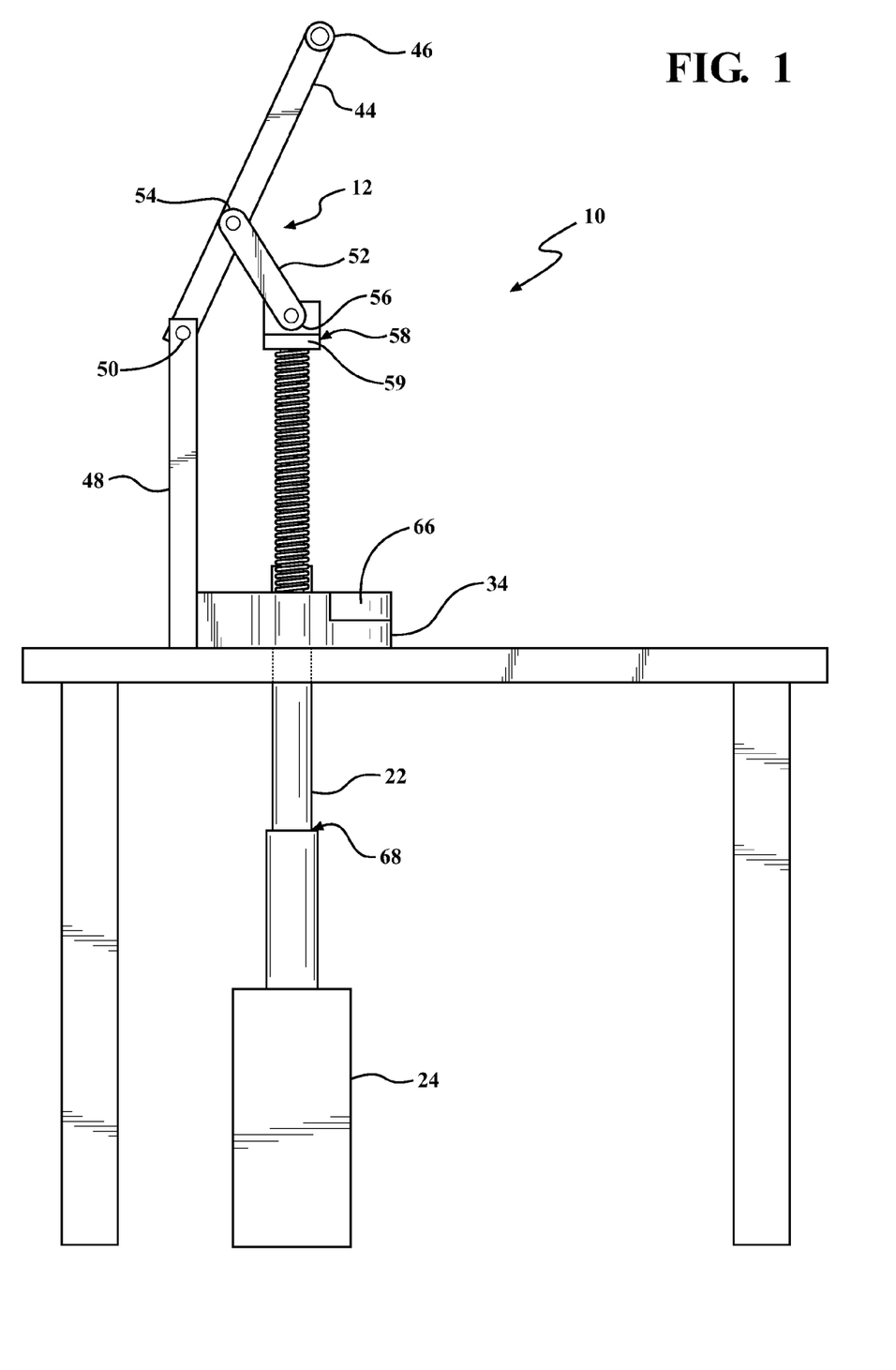
FIG. 1 is a side view of a sharp extractor constructed in accordance with one aspect of the invention.
Figure 2:
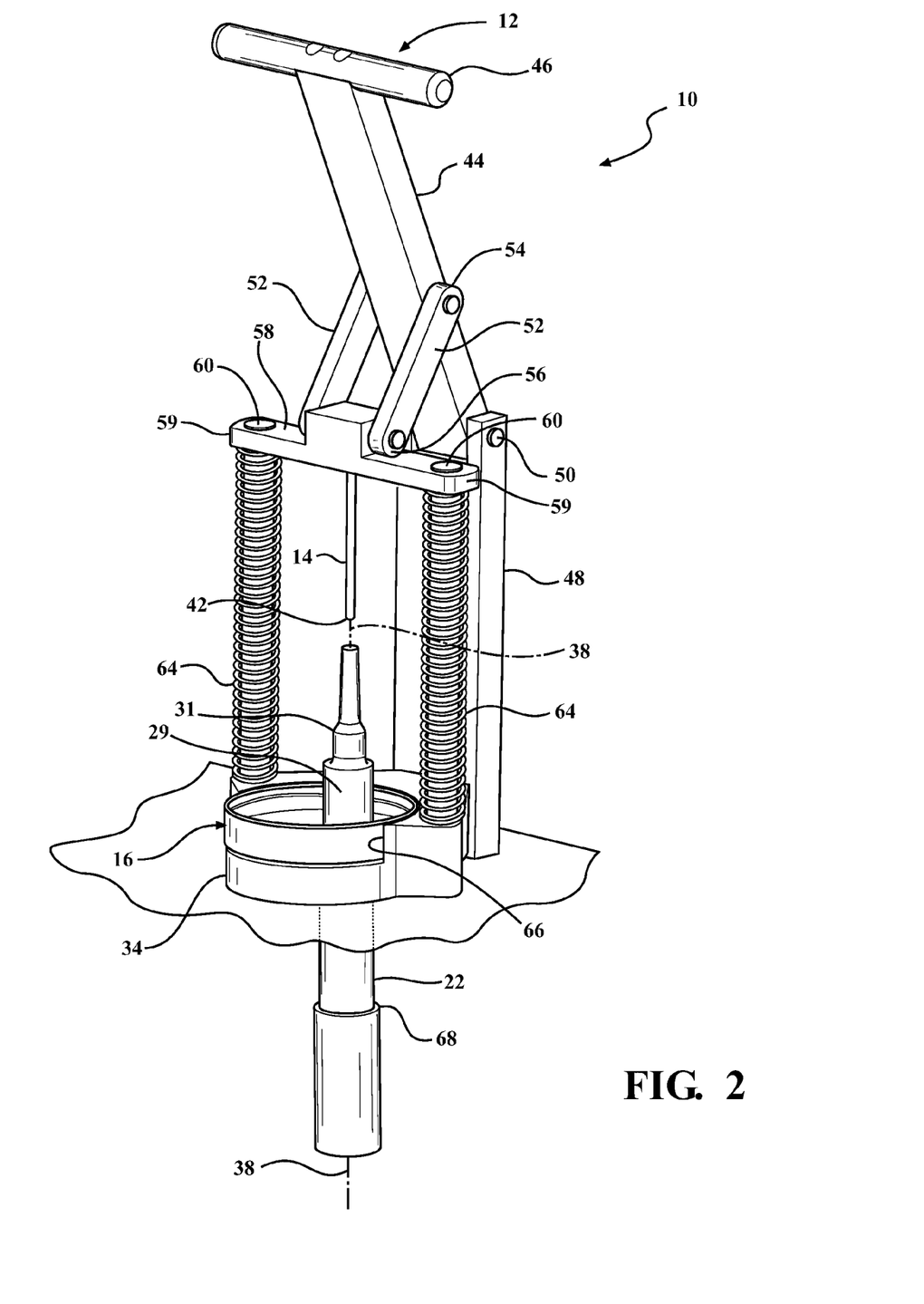
FIG. 2 is a perspective view of the sharp extractor of FIG. 1 shown in a disengaged state.
Figure 3:
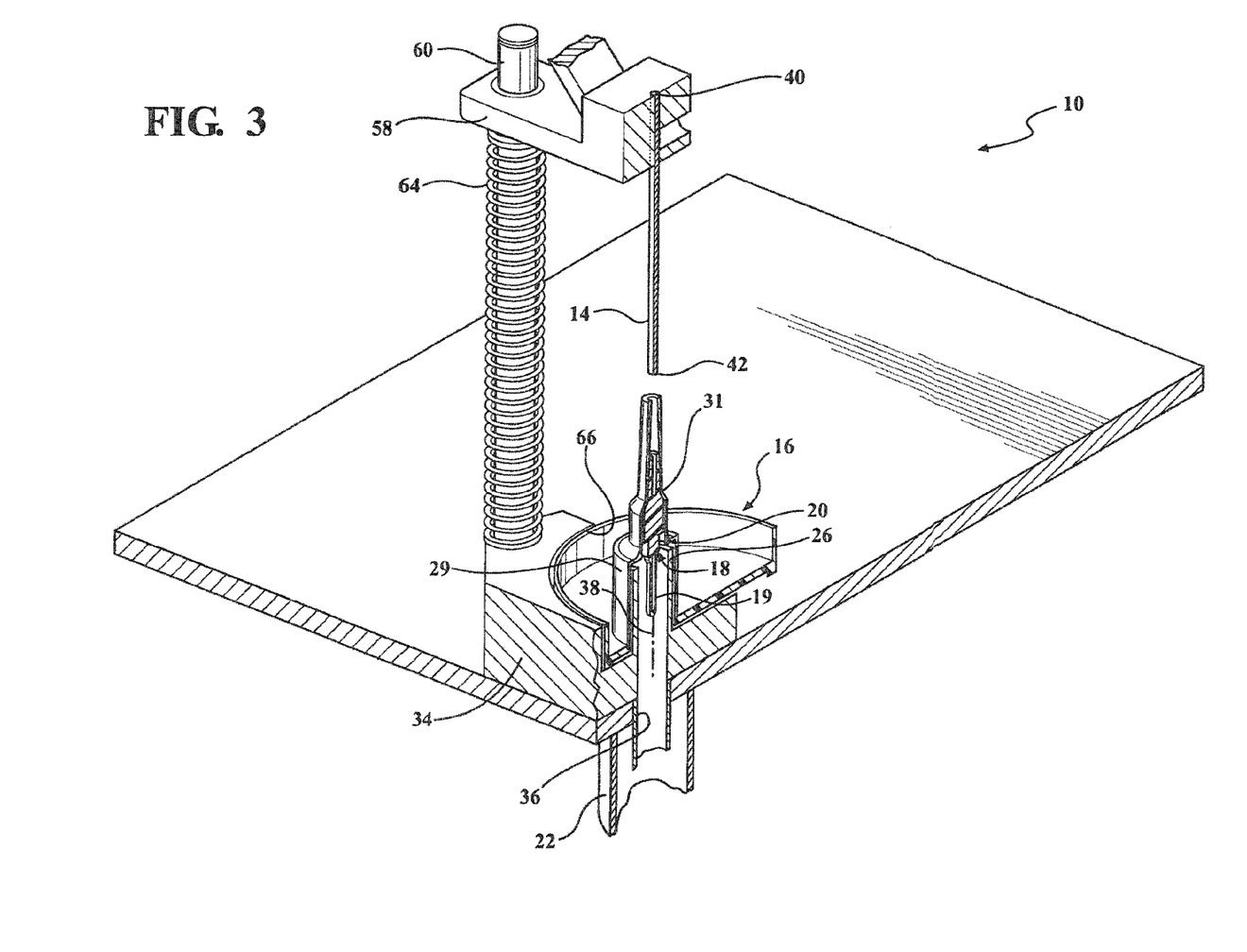
FIG. 3 is an enlarged partial cross-sectional perspective view of the sharp extractor of FIG. 1 shown in a disengaged state.

The actuator 12 is shown as having a manually actuatable lever assembly 44 operably connected to the ram 14 to facilitate moving the ram 14 between the disengaged and engaged positions. The lever assembly 44 is shown as having a handle 46 at one end and as being pivotally attached to a fixed, upright support member 48 at an opposite end, such as via a pin 50, by way of example and without limitation. The fixed support member 48 is shown as extending upwardly in fixed relation from the base 34. The lever assembly 44 is operably attached to the ram 14 via at least one, and shown as a plurality of pivotable link arms, referred to hereafter simply as links 52. As best shown in FIG. 2, each of the links 52 are generally parallel in mirrored relation with one another and are pivotably coupled at one end 54 to the lever assembly 44 between the opposite ends of the lever assembly 44 and pivotably coupled at an opposite end 56 to a cross member 58. The cross member 58 extends in generally parallel relation to the base 34 beyond the links 52 to opposite ends 59.

The ram 14 is fixed to the cross member 58 generally equidistantly between the opposite ends 59 of the cross member 58 in depending relation from the cross member 58. It should be recognized the ram 14 can be fixed to the cross member 58 via any suitable mechanical and/or weld and/or adhesive joint. The cross member 58 is supported for uniform, conjoint movement with the ram 14 adjacent its opposite ends 59 by upstanding guide members 60. The guide members 60 are shown as being fixed to the base 34 on opposite sides of the locator 26 and extend generally vertically upwardly from the base 34. The guide members 60 extend through respective through openings 62 of the cross member 58 adjacent the opposite ends 59 of the cross member 58 to allow for relative slidable movement between the cross member 58 and the guide members 60. Accordingly, the through openings 62 within the cross member 58 are sized for a loose or clearance fit about the guide members 60.

As best shown in FIG. 2, the lever assembly 44, cross member 58, and thus, ram 14, are biased to remain in the disengaged position by spring members 64, shown as being coil springs disposed about the upstanding guide members 60, by way of example and without limitation. The spring members 64 are provided having a predetermined length and spring rate to ensure the actuator 12 remains in the disengaged position absent an externally applied force to the lever assembly 44. Otherwise, when an operator applies a force to the lever assembly 44, the spring members 64 are readily compressed along the guide members 60 until the ram 14 reaches the fully deployed and engaged position, such as shown in FIG. 6. If desired, the spring members 64 can be provided to act as positive stop members, such that upon collapsing the springs 64 they reach a fully compressed state that prevents the cross member 58 and ram 14 from being moved further downwardly. Of course, upon fully depressing the lever assembly 44, the applied force can be removed from the lever assembly 44, whereupon the spring members 64 automatically bias the cross member 58 and ram 14 upwardly along the guide members 60 until they return to the disengaged position.

In use, an operator disposes the medical device 16 on the upstanding tubular locator 26, which, as discussed above, is sized for close receipt in the cylindrical recessed portion 29 of the lid portion 32. Upon locating the medical device 16 on the locator 26, the elongate sharp 18 is automatically aligned in coaxial alignment with the ram 14, as the ram 14 and locator 26 are coaxially aligned with one another. In addition to providing an alignment function, the locator 26 also provides rigid support against the recessed cylindrical portion 29 and the funnel-shaped portion 31 of the lid portion, which facilitates the sharp removal process, as discussed further below. In addition, although not necessary for alignment purposes, the locator 26 can be surrounded or partially surrounded by an axially offset, eccentric receptacle or wall 66 sized for close receipt of at least a portion of the lid assembly 30. With the wall 66 being in eccentric relation with the locator 26, an anti-rotation feature is provided that prevents the lid assembly 30 from rotating on the locator 26. This is made possible due to the sharp 18 being located on the lid portion 32 in off-center relation relative to a geometric center of the lid portion 32.

Figure 6A:
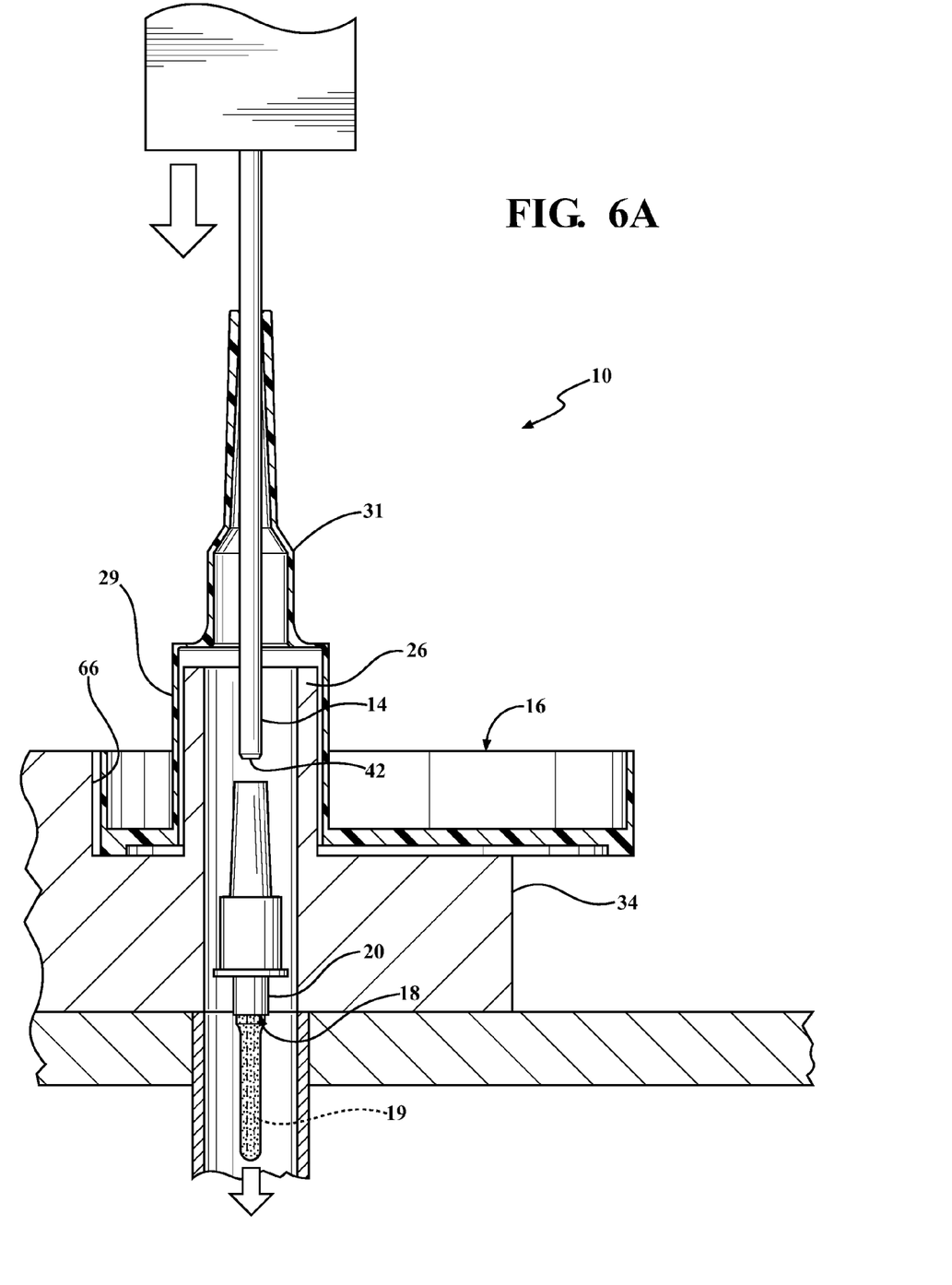
FIG. 6A is a view similar to FIG. 6 shown in a post-engaged state with a sharp dislodged from a medical device.

Upon locating the lid assembly 30 on the locator 26, the operator is free to actuate the extractor 10 with a single hand, while keeping the other hand free and clear from the extractor 10 and the lid assembly 30. Accordingly, the extractor 10 is suitable for use with a single hand. The operator actuates the extractor 10 by applying a sufficient force to the lever assembly 44 to overcome the bias imparted by the spring members 64. In doing so, the lever assembly 44 pivots relative to the upstanding support member 48 and causes the links 52 to pivot relative to the lever assembly 44 and cross member 58. In turn, the cross member 58 is driven and guided along the guide members 60 downwardly to the base 34 until the ram 14, moving conjointly with the cross member 58, reaches its fully engaged position. As the ram 14 is moving along the central axis 38, it is extended at least partially through the funnel-shaped portion 31 prior to engaging the needle assembly 18 and is then ultimately brought into forceful engagement with the needle assembly, shown as engaging the housing 20 of the needle assembly 18 (FIG. 6). The engagement of the ram 14 with the housing 20, with needle 19 fixed to the housing 20, causes the needle assembly 18 to move relative to the lid portion 32 axially through the tubular locator 26 under the force of the ram 14 until the needle assembly 18 becomes completely dislodged from the lid portion 32 (FIG. 6A). During forcible removal of the needle assembly 18, with the tubular locator 26 being located in a close fit within the recessed cylindrical portion 29 of the lid portion 32 directly beneath the funnel-shaped portion 31, the locator 26 acts to prevent the recessed cylindrical portion 29 and/or the funnel-shaped portion 31 from collapsing during the forceful extraction of the needle assembly 18 from the lid portion 32. Otherwise, without the rigid support provided by the locator 26 against the wall of the recessed cylindrical portion 29, the force generated in the extraction process necessary to remove the needle assembly 18 from the lid portion 32 could cause inadvertent collapsing of the recessed cylindrical portion and/or funnel-shaped portion 29, 31 of the lid portion 32, thereby compromising the extraction process.

Upon dislodging the needle assembly 18 from the lid portion 32, the needle assembly 18 falls through the through opening 36 in the base 34 and falls through the discharge chute 22 that extends from the through opening 36 of the base 34 toward the medical waste container 24. Preferably the discharge chute 22 extends fully into the medical waste container 24 to ensure the sharp 18 is maintained out of contact with the operator and external environment throughout the entire sharp removal process, thereby negating any opportunity for injury or contamination. To facilitate extending the discharge chute 22 into an opening the medical waste container 24, the discharge chute 22 can be provided with a telescoping feature 68, such as concentrically nested tubes, such that the tube of the discharge chute 22 can be telescopically extended and retracted to the desired length to accommodate medical waste containers 24 of different sizes.

The sharp extractor 10 can be fabricated from any suitable materials, including rigid plastics and metals. Desirably, the sharp extractor 10 can be readily cleaned and sterilized to prevent the spread of infectious bacteria, as is generally required in the medical arena. Further, it should be recognized that the sharp extractor 10 can be actuatable via other mechanisms than manual actuation, and that the actuation could be automated via electronic devices, hydraulic devices, pneumatic devices, or otherwise, if desired. With this, it should be understood that many modifications and variations of the present invention are possible in light of the above teachings. Accordingly, it is to be understood that the invention may be practiced otherwise than as specifically described, and that the scope of the invention is defined by any ultimately allowed claims.

What is claimed is:

1. A sharp extractor for removing a sharp from a medical device, comprising:
    a base having a through opening with a central axis;
    a tubular locator and a wall extending upwardly from said base, said tubular locator extending in coaxial alignment with said central axis of said through opening, said wall extending at least partially about said tubular locator in eccentric relation with said tubular locator;
    an elongate ram extending between first and second ends; and
    an actuator operably attached to said elongate ram, said ram being moveable in response to actuation of said actuator along said central axis from a disengaged position to an engaged position, said second end of said elongate ram being axially spaced from the sharp in said disengaged position and being engageable with said sharp when moved toward said engaged position whereupon said elongate ram causes the sharp to be separated from the medical device.

2. The sharp extractor of claim 1 further comprising a tubular discharge chute extending downwardly from said through opening of said base.

3. The sharp extractor of claim 1 wherein the actuator is operably attached to said first end of said elongate ram.

4. The sharp extractor of claim 1 wherein said actuator is spring biased.

5. The sharp extractor of claim 1 wherein said actuator includes a pivotable handle operably connected to said elongate ram via pivotable links.

6. A sharp extractor configured to remove a needle assembly from a lid assembly of a specimen reservoir assembly, said specimen reservoir assembly including a reservoir and said lid assembly, said lid assembly including said needle assembly releasably attached to a lid portion configured for attachment to said reservoir, said sharp extractor, comprising:
- a base having a through opening extending about a central axis;
- a tubular locator extending upwardly from said base in coaxial alignment with said central axis;
- an elongate ram;
- an actuator operably attached to said elongate ram, said elongate ram being moveable along said central axis from a disengaged position to an engaged position in response to actuation of said actuator, wherein said elongate ram is axially spaced from the needle assembly in said disengaged position and is engageable with the needle assembly when moved toward said engaged position wherein said elongate ram causes the needle assembly to be detached from the lid portion;
- a tubular discharge chute extending downwardly from said through opening of said base; and
- a waste container disposed at an end of said tubular discharge chute, with said waste container being configured to receive the needle assembly upon passing through said tubular discharge chute.

7. The sharp extractor of claim 6 wherein the elongate ram has opposite first and second ends, said actuator being operably attached to said first end of said elongate ram and said second end being configured for engagement with the needle assembly.

* * * * *